US010258933B2

(12) United States Patent
Yajima et al.

(10) Patent No.: US 10,258,933 B2
(45) Date of Patent: Apr. 16, 2019

(54) ZEOLITE MEMBRANE HAVING OXYGEN EIGHT-MEMBERED RINGS, METHOD FOR MANUFACTURING ZEOLITE MEMBRANE AND METHOD FOR EVALUATING ZEOLITE MEMBRANE HAVING OXYGEN EIGHT-MEMBERED RINGS

(71) Applicant: NGK Insulators, Ltd., Nagoya (JP)

(72) Inventors: Kenji Yajima, Nagoya (JP); Takeshi Hagio, Nagoya (JP); Makoto Miyahara, Nagoya (JP); Tetsuya Uchikawa, Nagoya (JP); Naoko Inukai, Nagoya (JP); Makiko Ichikawa, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 595 days.

(21) Appl. No.: 14/858,201

(22) Filed: Sep. 18, 2015

(65) Prior Publication Data

US 2016/0008771 A1    Jan. 14, 2016

Related U.S. Application Data

(63) Continuation of application No. PCT/JP2014/059349, filed on Mar. 28, 2014.

(30) Foreign Application Priority Data

Mar. 29, 2013   (JP) ................................. 2013-074930

(51) Int. Cl.
*B01D 53/22*     (2006.01)
*B01D 63/06*     (2006.01)
(Continued)

(52) U.S. Cl.
CPC ......... *B01D 71/028* (2013.01); *B01D 53/228* (2013.01); *B01D 63/066* (2013.01);
(Continued)

(58) Field of Classification Search
CPC .......................... B01D 71/028; B01D 67/0051; B01D 63/066; B01D 65/10; B01D 53/228;
(Continued)

(56) References Cited

U.S. PATENT DOCUMENTS

| 6,689,195 B1 | 2/2004 | Anthonis et al. |
| 2005/0139065 A1* | 6/2005 | Miller .................. B01D 53/228 95/45 |

(Continued)

FOREIGN PATENT DOCUMENTS

| JP | H08-266876 A | 10/1996 |
| JP | 2002-537990 A | 11/2002 |

(Continued)

OTHER PUBLICATIONS

Francois Bonhomme, et al., "$CO_2$ Selectivity and Lifetimes of High Silica ZSM-5 Membranes," *Microporous and Mesoporous Materials*, vol. 66, No. 2-3, Dec. 5, 2003, pp. 181-188.
(Continued)

*Primary Examiner* — Vishal V Vasisth
(74) *Attorney, Agent, or Firm* — Burr & Brown, PLLC

(57) ABSTRACT

Provided is a zeolite membrane manufactured by: subjecting a porous body to heat treatment at 400° C. or more in the presence of oxygen as pretreatment, before adhering zeolite seed crystals to a surface of the porous body; storing the porous body under an environment of humidity of 30% or more for 12 hours or more after the heat treatment; and subsequently adhering the zeolite seed crystals to the porous body. The zeolite membrane having oxygen eight-membered rings, which is manufactured by subjecting the porous body to the heat treatment, provides a value that is obtained by dividing a permeance of $CF_4$ by a permeance of $CO_2$ to be 0.015 or less, and has fewer defects.

13 Claims, 3 Drawing Sheets

(51) Int. Cl.
  *B01D 65/10* (2006.01)
  *B01D 67/00* (2006.01)
  *B01D 71/02* (2006.01)
  *G01N 15/08* (2006.01)

(52) U.S. Cl.
  CPC ......... *B01D 65/10* (2013.01); *B01D 67/0051* (2013.01); *G01N 15/08* (2013.01); *B01D 2323/08* (2013.01); *B01D 2323/24* (2013.01); *B01D 2323/36* (2013.01); *B01D 2325/20* (2013.01)

(58) Field of Classification Search
  CPC ............ B01D 2323/08; B01D 2323/24; B01D 2323/36; B01D 2325/20; G01N 15/08
  See application file for complete search history.

(56) References Cited

U.S. PATENT DOCUMENTS

| | | |
|---|---|---|
| 2009/0007780 A1 | 1/2009 | Yajima et al. |
| 2009/0011926 A1 | 1/2009 | Yajima et al. |
| 2010/0298115 A1 | 11/2010 | Yajima et al. |
| 2013/0064747 A1 | 3/2013 | Zhou et al. |

FOREIGN PATENT DOCUMENTS

| | | |
|---|---|---|
| JP | 2003-144871 A | 5/2003 |
| JP | 2003-210950 A | 7/2003 |
| JP | 2004-083375 A | 3/2004 |
| JP | 2013-226535 A | 11/2013 |
| WO | 2007/105407 A1 | 9/2007 |
| WO | 2007/119286 A1 | 10/2007 |

OTHER PUBLICATIONS

P. Kumar, et al., "Ordered Mesoporous Membranes: Effects of Support and Surfactant Removal Conditions on Membrane Quality," *Journal of Membrane Science*, vol. 279, No. 1-2, Aug. 1, 2006, pp. 539-547.

Extended European Search Report (Application No. 14775879.1) dated Oct. 21, 2016.

Den Exter, M.J., et al., "Separation of Permanent Gases on the All-Silica 8-Ring Clathrasil DD3R," *Studies in Surface Science and Catalysis*, vol. 84, dated 1994 (8 pages).

Zhang, Yanfeng, et al., "Blocking defects in SAPO-34 membranes with cyclodextrin," *Journal of Membrane Science*, vol. 358, dated 2010 (7 pages).

European Office Action, European Application No. 14775879.1, dated Nov. 26, 2018 (4 pages).

\* cited by examiner

ZEOLITE MEMBRANE HAVING OXYGEN EIGHT-MEMBERED RINGS, METHOD FOR MANUFACTURING ZEOLITE MEMBRANE AND METHOD FOR EVALUATING ZEOLITE MEMBRANE HAVING OXYGEN EIGHT-MEMBERED RINGS

This application is a CON of PCT/JP2014/059349, filed Mar. 28, 2014.

BACKGROUND OF THE INVENTION

1. Field of the Invention

The present invention relates to a zeolite membrane having oxygen eight-membered rings, a method for manufacturing a zeolite membrane and a method for evaluating a zeolite membrane having oxygen eight-membered rings.

2. Description of Related Art

Recently, in order to collect only a specific component from a multicomponent mixture (a fluid mixture) selectively, ceramic filters have been used. The ceramic filters are superior to organic polymer filters in mechanical strength, durability, corrosion resistance and the like, and are preferably applied to removal of suspended substances, bacteria, powder dust or the like in liquid or gas, in a wide range of fields such as water treatment, exhaust gas treatment, food and medicine.

As such a filter, a filter obtained by forming a zeolite membrane on porous ceramics is known. Pores of zeolite can be classified by the number of oxygen atoms in their constituting parts into oxygen six-membered rings, oxygen eight-membered rings, oxygen ten-membered rings and the like. In particular, for separation of small-sized molecules such as water and carbon dioxide, a zeolite membrane which has pores of oxygen eight-membered rings and does not have any pore of the larger number of oxygen atoms (hereinafter, referred to as a zeolite membrane having oxygen eight-membered rings) is preferable, because of a relation between a molecular size and a zeolite pore diameter. As the zeolite membrane having oxygen eight-membered rings, an LTA type, a DDR type, a CHA type, an AEI type, an RHO type and the like can be exemplified.

Patent Document 1 discloses a DDR-type zeolite membrane which has a small and uniform membrane thickness and exhibits a large gas permeation amount.

Patent Document 2 discloses a dehydration method and a dehydration apparatus with a DDR-type zeolite membrane which is suitable for dehydrating acid solution.

Patent Document 3 discloses a gas separator with fewer defects.

Patent Document 4 discloses a zeolite membrane composite that contains a CHA-type zeolite. Further, Patent Document 5 discloses an LTA-type zeolite membrane.

CITATION LIST

Patent Documents

[Patent Document 1] WO 2007/105407 A
[Patent Document 2] WO 2007/119286 A
[Patent Document 3] JP-A-H8-266876
[Patent Document 4] JP-A-2013-226535
[Patent Document 5] JP-A-2003-210950

SUMMARY OF THE INVENTION

Problem to be Solved by the Invention

However, a zeolite membrane having oxygen eight-membered rings, which was produced according to the conventional techniques, could not sometimes exhibit a stable high separation performance depending on states of porous bodies on which the zeolite membranes are to be formed. For example, if evaluating a gas permeation performance of a DDR-type zeolite membrane that was produced according to the conventional technique, a ratio of ($CF_4$ permeance/$CO_2$ permeance) was sometimes high. Herein, since $CF_4$ is a molecule that is larger than DDR-type zeolite pores, the permeance of $CF_4$ represents the gas permeation performance of a membrane defect portion. Further, since $CO_2$ permeates both of DDR-type zeolite pores and defects, the permeance of $CO_2$ represents the gas permeation performance of the whole of the membrane. That is, it can be considered that, according to the conventional production method, the ratio of [$CF_4$ permeance/$CO_2$ permeance] is high, and defects are generated in the membrane at certain proportion or more. Thus, the membrane produced according to the conventional technique could not be sometimes used for the purpose which requires a high separation performance in the separation of mixed gas or mixed liquid.

Although Patent Document 1 discloses a DDR-type zeolite membrane which has a small and uniform membrane thickness, its defect amount is not evaluated with high precision, and the reduction of the defect amount may be insufficient. Patent Document 2 shows only a dehydration method and apparatus, and does not particularly specify any performance of a DDR-type zeolite membrane or its manufacturing method. In Patent Document 3, a substrate is subjected to heat treatment so as to remove an organic matter before forming a membrane, but the membrane to be formed on the substrate is metal, and a membrane formation approach includes alloying, so that Patent Document 3 cannot suggest the effect to the siliceous zeolite membrane which is to be formed by hydrothermal synthesis.

Patent Document 4 discloses a CHA-type zeolite membrane of which $SiO_2/Al_2O_3$ and air permeation amount are specified, but since oxygen and nitrogen, which are the main components of the air, are smaller than pore diameters of the CHA-type zeolite, and permeate both of pores and defects, a defect amount thereof is not evaluated with high precision, so that the reduction of the defect amount may be insufficient. Patent Document 5 discloses an LTA-type zeolite membrane that can be applied to a liquid mixture, but does not evaluate its detect amount with high precision, so that the reduction of the defect amount may be insufficient.

The present invention aims to provide a method for manufacturing a zeolite membrane with fewer defects, a zeolite membrane having oxygen eight-membered rings with fewer defects, and a method for evaluating a zeolite membrane having oxygen eight-membered rings which enables to evaluate its defects.

Means for Solving the Problem

The inventors of the present invention have found that a zeolite membrane with fewer defects can be manufactured by subjecting a porous body to heat treatment in the presence of oxygen as pretreatment, before adhering zeolite seed crystals to a surface of the porous body. That is, according to the present invention, a zeolite membrane having oxygen eight-membered rings, a method for manufacturing a zeolite membrane and a method for evaluating a zeolite membrane having oxygen eight-membered rings, which will be described below, are provided.

According to a first aspect of the present invention, a zeolite membrane having oxygen eight-membered rings is provided, wherein a value obtained by dividing a permeance of $CF_4$ by a permeance of $CO_2$ is 0.015 or less.

According to a second aspect of the present invention, the zeolite membrane having oxygen eight-membered rings according to the above-described first aspect is provided, wherein an $N_2$ permeance in a state of containing a structure directing agent is 0.001 $NL/(m^2 \cdot min \cdot kPa)$ or less.

According to a third aspect of the present invention, the zeolite membrane having oxygen eight-membered rings according to the above-described first or second aspects is provided, which is a DDR-type zeolite membrane or an AEI-type zeolite membrane.

According to a fourth aspect of the present invention, a method for manufacturing a zeolite membrane provided, including: subjecting a porous body to heat treatment at 400° C. or more in the presence of oxygen as pretreatment, before adhering zeolite seed crystals to a surface of the porous body; and subsequently adhering the zeolite seed crystals to the porous body so as to manufacture the zeolite membrane.

According to a fifth aspect of the present invention, the method for manufacturing a zeolite membrane according to the above-described fourth aspect is provided, including: storing the porous body under an environment of humidity of 30% or more for 12 hours or more after the heat treatment; and subsequently adhering the zeolite seed crystals to the porous body.

According to a sixth aspect of the present invention, the method for manufacturing a zeolite membrane according to the above-described fourth or fifth aspects is provided, including removing a structure directing agent from the zeolite membrane of which $N_2$ permeance in a state of containing the structure directing agent is 0.001 $NL/(m^2 \cdot min \cdot kPa)$ or less.

According to a seventh aspect of the present invention, the method for manufacturing a zeolite membrane according to any one of the above-described fourth to sixth aspects is provided, wherein the zeolite membrane is a zeolite membrane having oxygen eight-membered rings.

According to an eighth aspect of the present invention, the method for manufacturing a zeolite membrane according to the above-described seventh aspect is provided, wherein, after adhering 0.05 $g/m^2$ or more of zeolite seed crystals having oxygen eight-membered rings to the surface of the porous body on which the zeolite membrane having oxygen eight-membered rings is to be formed, the zeolite membrane having oxygen eight-membered rings is formed in raw material solution that contains: any of (a) a silica source and water, (b) a silica source, an alumina source and water, (c) an alumina source, a phosphorus source and water, and (d) a silica source, an alumina source, a phosphorus source and water; and the structure directing agent.

According to a ninth aspect of the present invention, the method for manufacturing a zeolite membrane according to the above-described seventh or eighth aspects is provided, wherein the zeolite seed crystals having oxygen eight-membered rings, of which average particle diameter ranges from 1.5 times to 3.0 times of an average pore diameter on the surface of the porous body on which the zeolite membrane having oxygen eight-membered rings is to be formed, are adhered to the surface of the porous body so as to form the zeolite membrane having oxygen eight-membered rings.

According to a tenth aspect of the present invention, the method for manufacturing a zeolite membrane according to any one of the above-described seventh to ninth aspects is provided, wherein the average pore diameter on the surface of the porous body on which the zeolite membrane having oxygen eight-membered rings is to be formed ranges from 70 nm to 150 nm, and the average particle diameter of the zeolite seed crystals having oxygen eight-membered rings ranges from 105 nm to 450 nm.

According to an eleventh aspect of the present invention, the method for manufacturing a zeolite membrane according to any one of the above-described fourth to tenth aspects is provided, wherein the zeolite membrane is a DDR-type zeolite membrane.

According to a twelfth aspect of the present invention, the method for manufacturing a zeolite membrane according to any one of the above-described fourth to tenth aspects is provided, wherein the zeolite membrane is an AEI-type zeolite membrane.

According to a thirteenth aspect of the present invention, a method for evaluating a zeolite membrane having oxygen eight-membered rings is provided, wherein defects of the zeolite membrane having oxygen eight-membered rings are evaluated by a value that is obtained by dividing a permeance of $CF_4$ by a permeance of $CO_2$.

Effect of the Invention

According to the method for manufacturing a zeolite membrane of the present invention, a zeolite membrane with significantly few defects can be manufactured. Therefore, if this zeolite membrane is used to separate mixed gas or mixed liquid which contains both of smaller molecules and larger molecules than zeolite pores, a permeation amount of large molecules that should not originally permeate the zeolite membrane can be reduced.

DETAILED DESCRIPTION OF THE INVENTION

Figure 1:
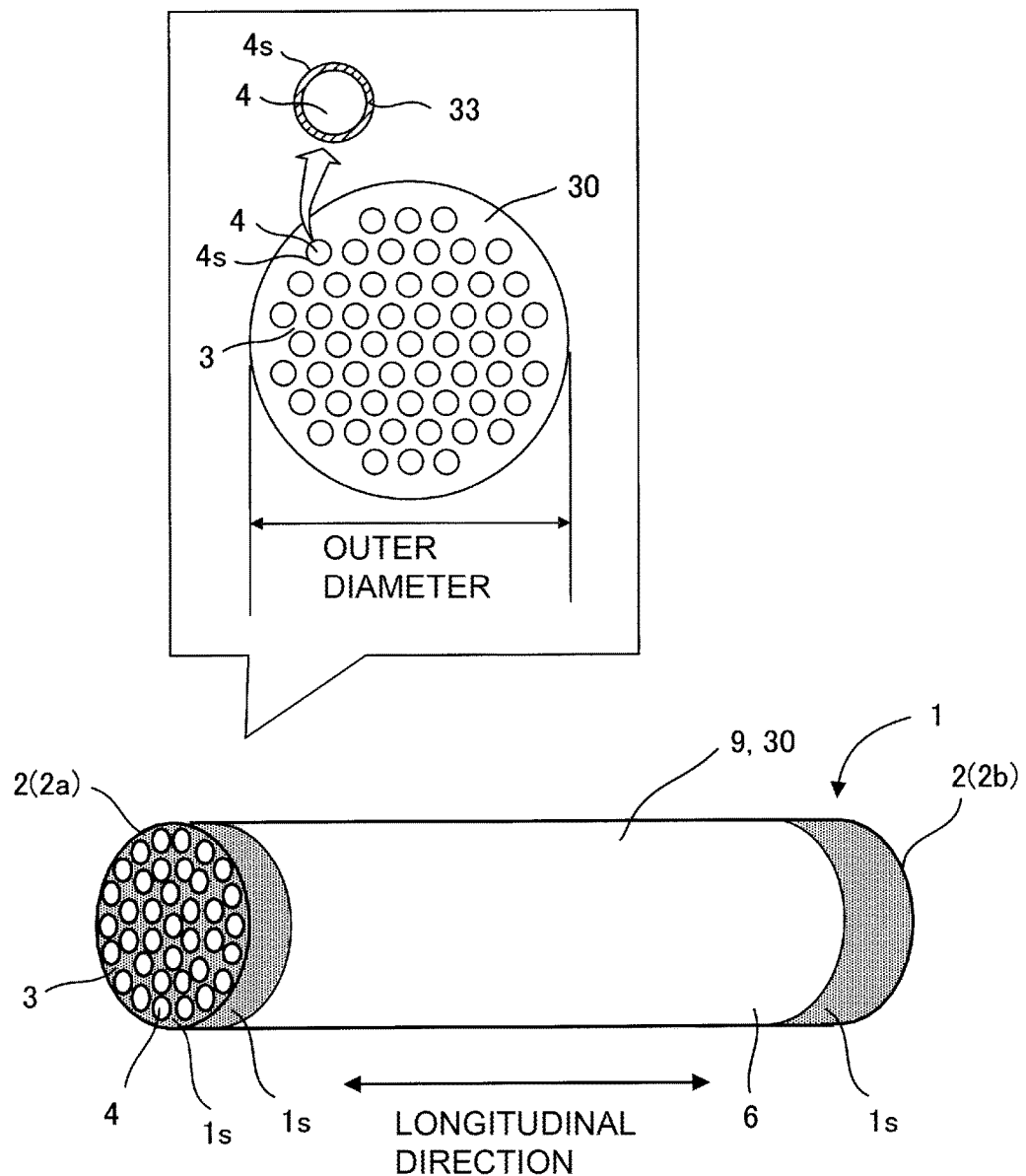
FIG. 1 is a drawing that illustrates one embodiment of a monolith-type separation membrane structure provided with a zeolite membrane according to the present invention.

Hereinafter, an embodiment of the present invention will be described with reference to the drawings. The present invention is not limited to the following embodiment, and changes, modifications and improvements may be added, as long as not departing from the scope of the present invention.

(1) Outline

A method for manufacturing a zeolite membrane of the present invention includes: subjecting a porous body to heat treatment at 400° C. or more in the presence of oxygen as pretreatment, before adhering zeolite seed crystals to a surface of the porous body; and subsequently adhering the zeolite seed crystals to the porous body so as to manufacture the zeolite membrane. Further, it is preferable to store the porous body under an environment of humidity of 30% or more for 12 hours or more after the heat treatment, and subsequently attach the zeolite seed crystals to the porous body. By carrying out such treatment before adhering the zeolite seed crystals to the porous body, impurities that stick to the porous body before the seeding can be removed after the firing, whereby the zeolite membrane with fewer defects can be manufactured.

The above-described method for manufacturing the zeolite membrane can be applied to various kinds of zeolite membranes, and can be applied to, for example, a zeolite membrane having oxygen eight-membered rings, more specifically, a DDR-type zeolite membrane and an AEI-type zeolite membrane.

The zeolite membrane having oxygen eight-membered rings of the present invention provides a value, which is obtained by dividing a permeance of $CF_4$ by a permeance of $CO_2$, to be 0.015 or less. The permeance denotes a value that is obtained by dividing a permeation amount of a membrane per unit time by a unit membrane area and further dividing it by differential pressure of a permeated component. The differential pressure of a permeated component denotes a difference in partial pressure of the permeated component between a first face on one side and a second face on the other side of the zeolite membrane having oxygen eight-membered rings. At the time of measuring the permeance, pressure of each face of the zeolite membrane having oxygen eight-membered rings is not limited particularly, but is preferably 1 MPa or less, normally.

In the zeolite membrane having oxygen eight-membered rings, $CF_4$ does not permeate pores of the zeolite membrane, but permeates only defects. Further, $CO_2$ permeates both of pores and defects of the zeolite membrane. Thus, a value of (permeance of $CF_4$)/(permeance of $CO_2$) serves as an indicator for detecting defects of the zeolite membrane. By using the method for manufacturing a zeolite membrane of the present invention, the zeolite membrane with fewer defects can be manufactured, so that the zeolite membrane having oxygen eight-membered rings of the present invention has the value of (permeance of $CF_4$)/(permeance of $CO_2$) of 0.015 or less. That is, defect portions other than the zeolite pores which $CF_4$ can permeate are significantly small, and permeation of organic solvent by passing through the defects other than the zeolite pores is also small. For example, if the value of (permeance of $CF_4$)/(permeance of $CO_2$) is 0.015 or less, when acetic acid solution of 90% is separated at 90° C., an acetic acid concentration on a membrane permeated side becomes 1% or less, whereby the zeolite membrane can exhibit a high-precision separation performance that can be applied to a wide variety of purposes.

In order to obtain such a zeolite membrane with fewer defects, the zeolite membrane is preferably formed on the porous body, after subjecting the porous body to the heat treatment as described above and storing the porous body under an environment of humidity of 30% or more. Then, in the case of forming the zeolite membrane by adhering the zeolite seed crystals to the porous body, an $N_2$ permeance in a state of containing a structure directing agent before removing the structure directing agent is preferably 0.001 $NL/(m^2 \cdot min \cdot kPa)$ or less, and more preferably 0.0003 $NL/(m^2 \cdot min \cdot kPa)$ or less. If the $N_2$ permeance in the state of containing the structure directing agent before removing the structure directing agent is within such a range, the zeolite membrane with fewer defects can be obtained after removing the structure directing agent. Hereinafter, the zeolite membrane of the present invention, a ceramic separation membrane structure including the same and the method for manufacturing the zeolite membrane will be described specifically.

(2) Zeolite Membrane and Ceramic Separation Membrane Structure

In FIG. 1, one embodiment of a ceramic separation membrane structure 1 that is provided with the zeolite membrane having oxygen eight-membered rings of the present invention (for example, a DDR-type zeolite membrane) is illustrated.

The ceramic separation membrane structure 1 (also called solely as separation membrane structure) includes a ceramic porous body 9 (also called solely as porous body) and a zeolite membrane 33 (or called as separation membrane) that is arranged on the ceramic porous body 9.

A shape of the porous body 9 is not limited particularly, and a shape that is generally called as a monolith type can be used. The monolith-type porous body 9 has a partition wall 3 made of porous medium in which many pores are formed, as shown in FIG. 1, and cells 4 that serve as through channels for fluid is formed with the partition wall 3. On an inner wall surface 4s of the cells 4, the zeolite membrane 33 is formed.

In the present specification, the porous body 9 denotes a substrate 30, but in the case where plural layers with different average particle diameters are provided on the substrate 30, the porous body 9 is a substrate 30 inclusive of the layers.

(Substrate and Porous Body)

A material of the substrate 30 is preferably porous ceramics. More preferably, aggregate particles are alumina ($Al_2O_3$), titania ($TiO_2$), mullite ($Al_2O_3 \cdot SiO_2$), potsherd and cordierite ($Mg_2Al_4Si_5O_{18}$) or the like. Among them, alumina is further preferable because its raw material (aggregate particles) with controlled particle diameters is easily available; a stable kneaded material can be formed; and its corrosion resistance is high.

A whole shape and a size of the substrate 30 are not particularly limited as long as they do not prevent its separation function. As the whole shape, for example, a round pillar shape, a square pillar shape (cylindrical shape of which cross section crossing its central axis orthogonally is square), a triangle pillar shape (cylindrical shape of which cross section crossing its central axis orthogonally is triangular) and the like are exemplified. Among them, the round pillar shape is preferable because it makes extrusion molding easier; causes less firing deformation; and facilitates sealing with a housing. In the embodiment shown in FIG. 1, the substrate 30 is round pillar-shaped, and has an outer peripheral surface 6.

In the case of using the substrate 30 for microfiltration or ultrafiltration, the substrate 30 preferably has a round pillar shape, of which diameter (outer diameter) of its cross section that orthogonally crosses its central axis ranges from 30 mm to 220 mm, and of which length in a direction of the central axis (longitudinal direction) ranges from 150 mm to 2000 mm. That is, as one embodiment of the substrate 30, a monolith type (monolith shape) is exemplified. The "monolith type" denotes a shape in which plural cells are formed from one end face to the other end face in the longitudinal direction, or a honeycomb shape. Alternatively, the substrate 30 may have a hollow cylindrical shape.

The substrate 30 in the embodiment shown in FIG. 1 has the plural cells 4, which are sectioned by the porous partition wall 3 from one end face 2a to the other end face 2b in the longitudinal direction, and serve as the through channel for the fluid. The substrate 30 has the 30 to 2500 cells 4 which run through the substrate 30 between both end sides in the longitudinal direction and are parallel with the longitudinal direction.

As a cross-sectional shape of the cell 4 of the substrate 30 (shape of a cross section that orthogonally crosses the direction in which the cell 4 extends), for example, a round shape, an elliptical shape, polygon shapes and the like can be exemplified, and as the polygon shapes, a square shape, a pentagon shape, a hexagon shape, a triangle shape and the like can be exemplified. Incidentally, the direction in which the cells 4 extend is the same as the direction of the central axis, in the case where the substrate 30 has the round pillar shape.

In the case where the cross-sectional shape of the cell 4 of the substrate 30 is a circular shape, a diameter of the cell 4 preferably ranges from 1 mm to 5 mm. If the diameter is 1 mm or more, a membrane area can be secured sufficiently. If the diameter is 5 mm or less, strength thereof can be sufficient.

On the substrate 30, the plural layers with the different average particle diameters can also be provided. More specifically, on the substrate 30, an intermediate layer and a surface layer with small average particle diameters can also be laminated. In the case of providing the intermediate layer and the surface layer, the porous body 9 is meant to include them.

A surface of the porous body 9 on which the zeolite membrane is to be formed preferably has an average pore diameter ranging from 70 nm to 150 nm. The average pore diameter more preferably ranges from 70 nm to 120 nm, and further preferably ranges from 80 nm to 120 nm. These ranges of the average pore diameter are particularly preferable in the case of forming the thin zeolite membrane (with a membrane thickness of, for example, 10 µm or less). If the average pore diameter on the surface of the substrate 30 is 70 nm or more, a permeance of a permeation separation component in the substrate 30, which is separated by the zeolite membrane 33, is high, and a permeation flow rate per unit time can be sufficient. On the other hand, if the average pore diameter is 150 nm or less, the membrane thereon can be formed to be thin and uniform easily.

Further, a porosity of a whole of the porous body 9 preferably ranges from 25% to 50%. The porosity more preferably ranges from 30% to 50%, and further preferably ranges from 30% to 45%. The average pore diameter and the porosity are values that are measured by a mercury porosimeter.

On both end faces 2 and 2 of the substrate 30, seal portions is are preferably provided. Such provision of the seal portions 1s can prevent that a part of a mixture directly inflows from the end face 2 of the substrate 30 into an inside of the substrate 30 without passing through the zeolite membrane 33, and is mixed with gas or the like that passes through the zeolite membrane 33 so as to be discharged from the outer peripheral surface 6. As a material of the seal portion 1s, for example, glass and metal can be exemplified.

(Zeolite Membrane)

The zeolite membrane 33 (separation membrane) that is manufactured by the method for manufacturing a zeolite membrane of the present invention has the pores derived from their crystal structures, of which pore diameters are smaller than the pore diameters on the surface of the porous body 9 (the substrate 30, or, if providing the intermediate layer and the surface layer, including them), and is arranged on the wall surfaces (inner wall surfaces 4s) in the cells 4. Alternatively, the zeolite membrane 33 may be arranged on the outer peripheral surface of the hollow cylindrical substrate 30.

As the zeolite membrane 33, zeolite having a crystal structure of LTA, MFI, MOR, FER, FAU, DDR, CHA, BEA, AEI or the like can be used.

As the zeolite membrane having oxygen eight-membered rings, which is manufactured by the method for manufacturing a zeolite membrane of the present invention, and of which value obtained by dividing the permeance of $CF_4$ by the permeance of $CO_2$ is 0.015 or less, those of DDR, CHA, LTA, AEI and the like are exemplified. As the zeolite membrane having oxygen eight-membered rings, which is manufactured by the method for manufacturing a zeolite membrane of the present invention, a DDR-type zeolite membrane is particularly preferable. In particular, in a case where the zeolite membrane 33 is a DDR-type zeolite membrane, the zeolite membrane 33 can be utilized also as a gas separation membrane that is used for separating carbon dioxide selectively.

(3) Manufacturing Method (3-1) Substrate and Porous Body

Next, a method for manufacturing the separation membrane structure 1 which uses the monolith-type substrate 30 will be described. Firstly, a raw material of the porous body 9 is formed. For example, a vacuum extruder is used for the extrusion forming. Thereby, the monolith-type unfired substrate 30 that has the cells 4 can be obtained. Besides, press molding, slip casting and the like can be adopted, from which appropriate selection can be made. Thereafter, the unfired substrate 30 is subjected to a firing process, in which the substrate 30 is fired at, for example, 900° C. to 1450° C. Incidentally, the plural layers with different average particle diameters may be provided on the substrate 30 subsequently. In the case of providing the plural layers with different average particle diameters on the substrate 30, the porous body 9 is meant to include those layers.

After the firing process, before adhering the zeolite seed crystals to the porous body 9, the porous body 9 is subjected to heat treatment at 400° C. or more in the presence of oxygen as pretreatment. The heat treatment as the pretreatment is a process that is different from the firing process for firing the unfired porous body 9, and is carried out after the firing process. Carrying out the heat treatment before adhering the zeolite seed crystals means adhering the zeolite seed crystals without carrying out any process other than storing (for example, cut-off, sealing application, gas permeation amount measurement, water permeation amount measurement or the like) after completing the heat treatment. The temperature of the heat treatment preferably ranges from 400° C. to 900° C., and more preferably ranges from 500° C. to 800° C. It is considered that, by carrying out such heat treatment, the surface of the porous body 9 can be cleaned.

Then, after the heat treatment, the porous body 9 is preferably stored under an environment at humidity of 30% or more for 12 hours or more. The porous body 9 is stored preferably at the humidity ranging from 30% to 90%, and more preferably at the humidity ranging from 40% to 90%. Moreover, the porous body 9 is stored preferably for 12 hours to one year, and more preferably for 24 hours to 30 days. It is considered that, by storing the porous body 9 under such an environment, the zeolite seed crystals can be adhered to the surface of the porous body 9 easily. After such storing, the zeolite seed crystals are adhered to the substrate.

(3-2) Zeolite Membrane

Next, the zeolite membrane 33 is formed on the inner wall surface 4s of the cell 4. The zeolite membrane 33 used in the present invention can be synthesized by a conventionally known method.

Figure 2:
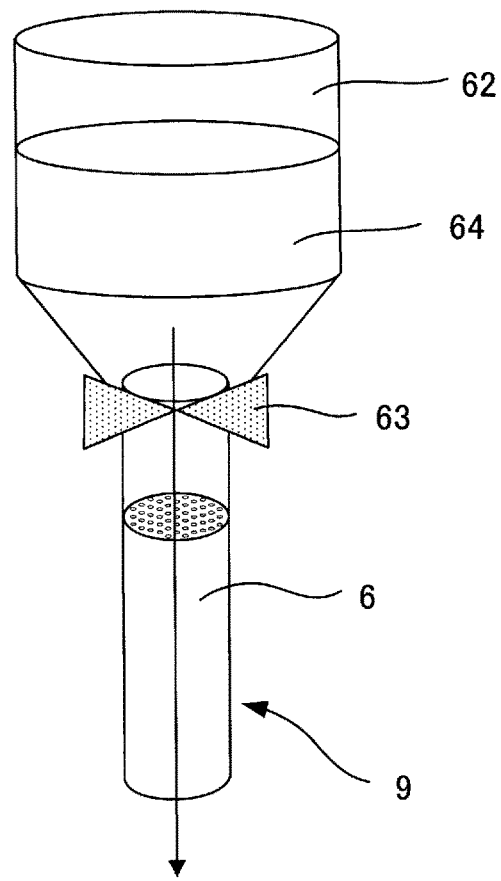
FIG. 2 is a schematic diagram that illustrates a state of pouring seeding slurry in a particle adhering process.

Firstly, the zeolite seed crystals are applied to the porous body 9 (substrate 30). An average particle diameter of the seed crystals preferably ranges from 105 nm to 450 nm. Incidentally, the average particle diameter denotes a value measured by laser diffraction. FIG. 2 illustrates one embodiment of seeding by a flow-down method. The porous body 9 is fixed to a lower end of a wide-mouth funnel 62, and seeding slurry 64 is poured from above of the porous body 9 by opening a cock 63 and is allowed to pass through insides of the cells 4, whereby the zeolite seed crystals can be adhered.

In the case of forming the zeolite membrane having oxygen eight-membered rings, more than 0.05 g/m² of the zeolite seed crystals having oxygen eight-membered rings are preferably adhered to the surface of the porous body 9. Further, it is further preferable that more than 0.5 g/m² of the zeolite seed crystals are adhered. According to these ranges, defects are not likely to be generated in the zeolite membrane having oxygen eight-membered rings.

The zeolite seed crystals having oxygen eight-membered rings, of which average particle diameter ranges from 1.5 times to 3.0 times of the average pore diameter on the surface of the porous body 9 on which the zeolite membrane having oxygen eight-membered rings is to be formed, are preferably adhered to the surface of the porous body 9. More preferably, the average particle diameter ranges from 1.5 times to 2.5 times of the average pore diameter. According to these ranges, defects are not likely to be generated in the zeolite membrane having oxygen eight-membered rings. In the case of less than 1.5 times, the seed crystals that enter the pores are increased, so that the zeolite membrane which is finally obtained may be thickened. Moreover, in the case of more than 3.0 times, the seed crystals that enter the pores are decreased significantly, but an area of a part to which the seed crystal is not adhered is increased relatively, and defects may be increased accordingly.

It is preferable that the average pore diameter on the surface of the porous body 9 which on which the zeolite membrane having oxygen eight-membered rings is to be formed ranges from 70 nm to 150 nm, and the average particle diameter of the zeolite seed crystals having oxygen eight-membered rings ranges from 105 nm to 450 nm. The average pore diameter on the surface of the porous body 9 more preferably ranges from 70 nm to 120 nm, and further preferably ranges from 80 nm to 120 nm. The average particle diameter of the zeolite seed crystals having oxygen eight-membered rings more preferably ranges from 105 nm to 360 nm, and further preferably ranges from 120 nm to 360 nm. According to these ranges, defects are not likely to be generated in the zeolite membrane having oxygen eight-membered rings.

Figure 3:
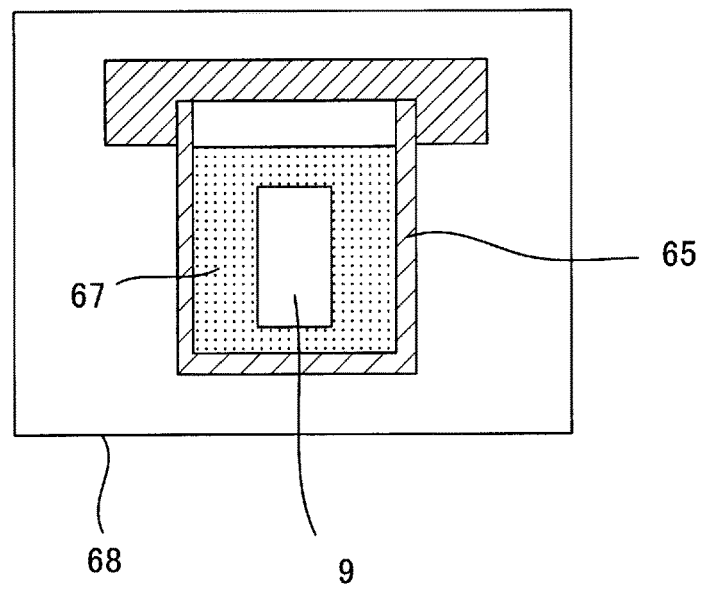
FIG. 3 is a schematic diagram that illustrates one embodiment of a membrane formation process for forming the zeolite membrane on a porous body by hydrothermal synthesis.

After adhering the zeolite seed crystals, raw material solution (sol 67) that contains: any of (a) a silica source and water, (b) a silica source, an alumina source and water, (c) an alumina source, a phosphorus source and water, and (d) a silica source, an alumina source, a phosphorus source and water; and the structure directing agent is produced. Then, as shown in FIG. 3, after pouring the mixed raw material solution (sol 67) with the porous body 9 (substrate 30) in a pressure resistant container 65, they are put into a drier 68, and are subjected to heat treatment (hydrothermal synthesis) at 100° C. to 200° C. for 1 hour to 240 hours, thereby manufacturing the zeolite membrane 33 (containing the structure directing agent).

As the silica source, colloidal silica, tetraethoxysilane, water glass, silicon alkoxide, fumed silica, precipitated silica and the like are exemplified.

As the alumina source, aluminum salts such as aluminum hydroxide, sodium aluminate, aluminum sulfate, aluminum nitrate and aluminum chloride, alumina powder, colloidal alumina and the like are exemplified.

As the phosphorus source, phosphoric acid and the like are exemplified.

The structure directing agent is used for forming a pore structure of the zeolite. As the structure directing agent, which is not particularly limited, organic compounds such as tetraethylammonium hydroxide, tetraethylammonium bromide, 1-adamantanamine, tetrapropylammonium hydroxide, tetrapropylammonium bromide and tetramethylammonium hydroxide are exemplified.

Moreover, the raw material solution may contain an alkali source. As the alkali source, alkali metal such as sodium hydroxide, lithium hydroxide and potassium hydroxide, alkali earth metal such as magnesium hydroxide and calcium hydroxide, quaternary ammonium hydroxide, organic amine and the like are exemplified.

In the case of the zeolite membrane having oxygen eight-membered rings, for obtaining the zeolite membrane having oxygen eight-membered rings with fewer defects (finished product) after removing the structure directing agent, the $N_2$ permeance in the state of containing the structure directing agent before removing the structure directing agent is preferably 0.001 NL/($m^2$·min·kPa) or less, and more preferably 0.0003 NL/($m^2$·min·kPa) or less.

The porous body 9 on which the zeolite membrane 33 (containing the structure directing agent) is formed by the hydrothermal synthesis is washed with water or warm water at 80° C. to 100° C., and is taken out and dried at 80° C. to 100° C. Then, the porous body 9 is put into an electric furnace, and is heated in the atmosphere at 400° C. to 800° C. for 1 hour to 200 hours, thereby removing the structure directing agent in the pores of the zeolite membrane 33 by combustion. As described above, the zeolite membrane 33 can be formed.

The above-described method for manufacturing the zeolite membrane 33 can be applied to zeolite having crystal structures of DDR, LTA, MFI, MOR, FER, FAU, CHA, BEA, AEI and the like. Incidentally, the specific numerical ranges described for the case of the zeolite membrane having oxygen eight-membered rings are the ranges that are particularly preferable in the case of a zeolite membrane having oxygen eight-membered rings of DDR, CHA, LTA, AEI or the like.

(4) Method for Evaluating Zeolite Membrane Having Oxygen Eight-Membered Ring

Defects of the zeolite membrane having oxygen eight-membered rings (of DDR, CHA, LTA, AEI or the like) can be evaluated by a value that is obtained by dividing the permeance of $CF_4$ by the permeance of $CO_2$, that is, the value of (permeance of $CF_4$)/(permeance of $CO_2$). $CF_4$ does not permeate pores of the zeolite membrane having oxygen eight-membered rings, but permeates only defects thereof. Moreover, $CO_2$ permeates both of pores and defects of the zeolite membrane. Incidentally, another combination of gas can also be used for estimating a permeation performance and a separation performance of liquid with high precision, from the permeances of the gas, as long as the combination is composed of: the gas of which molecular diameter is larger than the pores; and the gas of which molecular diameter is smaller than the pores. Further, the permeation performance and the separation performance of the liquid can be estimated also with a combination of molecules that are smaller than the pores, although the precision thereof is lowered slightly. Herein, as the pore diameter of the zeolite, a pore diameter defined by IZA (International Zeolite Association) is preferably used, and as the molecular diameter of the gas, a kinetic diameter is preferably used. Moreover, in the case where the pore diameters of the zeolite include a shorter diameter and a longer diameter, a molecule of which molecular diameter is shorter than the shorter diameter is denoted as "a molecule that is smaller than the pores", and a molecule of which molecular diameter is longer than the longer diameter is denoted as "a molecule that is larger than the pores".

(5) Separation Method

Figure 4:
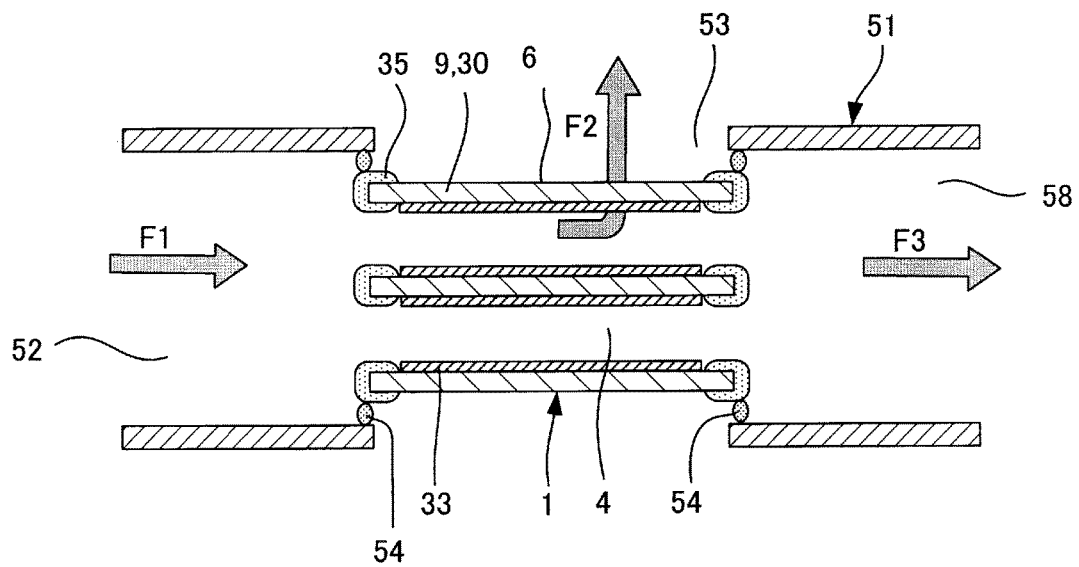
FIG. 4 is a schematic diagram that illustrates: an embodiment in which the monolith-type separation membrane structure is installed in a housing; and a cross-section which is parallel with a direction in which a cell of a ceramic separation membrane structure extends.

FIG. 4 illustrates an embodiment in which the separation membrane structure 1 is installed in a housing 51. As shown in FIG. 4, the separation membrane structure 1 is stored in the tubular housing 51 that has a fluid inlet 52 and fluid outlets 53 and 58.

When storing the separation membrane structure 1 in the housing 51, gaps between the separation membrane structure 1 and the housing 51 are preferably closed by sealing members 54 and 54 in both end portions of the separation membrane structure 1, as shown in FIG. 4. As the sealing members 54, which are not particularly limited, for example, an O-ring and the like are exemplified.

All of the fluid to be treated F1, which inflows from the fluid inlet 52 into the housing 51, inflows into the cells 4 of the separation membrane structure 1, and the fluid to be treated F1 that inflows into the cells 4 permeates the zeolite membrane 33 so as to become a treated fluid F2, and enters the porous body 9 (the substrate 30). Then, the treated fluid F2 outflows from the outer peripheral surface 6 of the porous body 9 to an outside of the porous body 9, and is discharged from the fluid outlet 53 to the outside (outer space). Further, the remaining fluid (fluid F3) can be discharged from the fluid outlet 58. Since the fluid F3 can be discharged from the fluid outlet 58, the operation can be made with a high flow rate of the fluid to be treated F1, and a permeation flow rate of the treated fluid F2 can be high.

EXAMPLES

Hereinafter, the present invention will be described in further detail by way of examples, but the present invention is not limited to these examples.

Examples 1 to 7 and Comparative Example 1

(1) Production of Substrate (Porous Body)

A porous body 9 was produced, and a zeolite membrane 33 was formed in its cells 4. Firstly, production of a substrate 30 will be described.

(Substrate)

To 100 parts by mass of alumina particles (aggregate particles) with an average particle diameter of 50 µm, 20 parts by mass of a sintering auxiliary agent (inorganic binder) was added, and further, water, a dispersing agent and a thickening agent were added, which were mixed and kneaded so as to prepare a kneaded material. The obtained kneaded material was subjected to extrusion forming, thereby producing the honeycomb-shaped unfired substrate 30.

Next, the substrate 30 was fired. Firing conditions were at 1250° C. and for 1 hour, and both speeds of temperature rising and temperature falling were 100° C./hour.

An outer shape of the substrate 30 was round pillar and had: an outer diameter of 30 mm; a cell inner diameter of 2.5 mm; the number of the cells of 61; and a length of 160 mm.

Next, onto cell inner surfaces of the substrate 30, alumina particles with an average particle diameter of 6 µm were laminated, and were fired at 1350° C. for 1 hour, thereby forming an intermediate layer. Further, alumina particles with an average particle diameter of 0.3 µm were laminated, and were fired at 1350° C. for 1 hour, thereby forming a surface layer. As described above, the porous body 9 having the intermediate layer and the surface layer formed on the cell inner surfaces of the substrate 30 was produced. A final cell inner diameter of the porous body 9 was 2.1 mm.

(Formation of Glass Seal)

Next, on both end faces 2a and 2b of the porous body 9, glass seals (the seal portions 1s) were provided so as not to close open ends of the cells 4.

(2) Heat Treatment of Porous Body

Before adhering zeolite seed crystals to the porous body 9, the porous body 9 was subjected to heat treatment at 400° C. or more in the presence of oxygen (in the air atmosphere in Examples 1, 4, 6 and 7, and in oxygen in Examples 2, 3 and 5) for 5 hours as pretreatment. Incidentally, in Comparative Example 1, the heat treatment was not carried out.

After the heat treatment, the porous body 9 was stored in a room at humidity of 40% or more for 12 hours or more. Alternatively, the porous body 9 was stored in a desiccator which is set at humidity of 25% or less. Specific conditions of the heat treatment and storage conditions are shown in Table 1.

(3A) Formation of DDR-type Zeolite Membrane

In Examples 1 to 7 and Comparative Example 1, a DDR-type zeolite membrane was formed as the zeolite membrane 33 on inner wall surfaces 4s of the cells 4 of the porous body 9.

(3A-1) Production of Seed Crystal

DDR-type zeolite crystal powder was manufactured based on a method for manufacturing a DDR-type zeolite, which is described in M. J den Exter, J. C. Jansen, H. van Bekkum, Studies in Surface Science and Catalysis vol. 84, Ed. by J. Weitkamp et al., Elsevier (1994)1159-1166 or JP-A-2004-083375, and the manufactured DDR-type zeolite crystal powder was used as it is, or was pulverized as necessary so as to be used as seed crystals. The seed crystals after the synthesis or the pulverization were dispersed into water, and coarse particles were removed as necessary, thereby producing seed crystal dispersion liquid.

(3A-2) Seeding (Particle Adhering Process)

The seed crystal dispersion liquid produced in (3A-1) was diluted with ethanol and adjusted so that a concentration of the DDR-type zeolite might be 0.09% by mass (a solid content concentration in slurry), and was stirred at 300 rpm by a stirrer, thereby obtaining seeding slurry solution (slurry 64). The porous body 9 was fixed to a lower end of a wide-mouth funnel, and 160 ml of the seeding slurry solution was poured from above of the porous body 9 so as to pass through insides of the cells 4. The insides of the cells of the porous body 9, through which the slurry 64 flowed down, were dried by through air drying under conditions of room temperature and a wind speed of 4 m/s for 20 minutes. The flow down of the slurry 64 and the through air drying were repeated twice, thereby obtaining a sample. After drying the sample, its microstructure was observed with an electron microscope. The DDR-type zeolite seed crystals were confirmed to be adhered to the surface of the porous body 9. The seed crystal diameter and the adhered amount of the adhered seed crystals and the pore diameter of the porous body and the value of (seed crystal diameter/pore diameter of the porous body) are shown in Table 1.

TABLE 1

| Sample | Heat Treatment of Porous Body Temperature [° C.] | Storage after Heat Treatment Storing Time at Humidity of 30% or more [hr] | Pore Diameter of Porous Body [nm] | Seed Crystal Diameter [nm] | Adhered Amount of Seed Crystal [g/m²] | Seed Crystal Diameter/Pore Diameter of Porous Body [—] |
|---|---|---|---|---|---|---|
| Comparative Example 1 | None | 0 | 116 | 240 | 0.48 | 2.1 |
| Example 1 | 400 | 0 | 116 | 240 | 0.51 | 2.1 |
| Example 2 | 500 | 0 | 73 | 205 | 0.51 | 2.8 |
| Example 3 | 400 | 24 or more | 73 | 240 | 0.10 | 3.3 |
| Example 4 | 500 | 24 or more | 87 | 240 | 0.09 | 2.8 |
| Example 5 | 500 | 24 or more | 73 | 199 | 0.51 | 2.7 |
| Example 6 | 500 | 16 | 116 | 205 | 0.09 | 1.8 |
| Example 7 | 500 | 24 or more | 73 | 199 | 0.48 | 2.7 |
| Example 8 | 500 | 24 or more | 116 | 340 | 0.25 | 2.9 |

(3A-3) Membranation (Membrane Formation Process)

After putting 6.8 g of ethylenediamine (produced by Wako Pure Chemical Industries, Ltd.) into a wide-mouthed bottle of 100 ml which is made of fluororesin, 1.07 g of 1-adamantanamine (produced by Aldrich) was added and dissolved so that a precipitation of the 1-adamantanamine might not remain. Then, 91 g of colloidal silica of 30% by mass (SNOWTEX S, produced by NISSAN CHEMICAL INDUSTRIES, LTD.) and 108 g of ion exchanged water were put into another container, and were stirred lightly. Thereafter, this obtained solution was added into the wide-mouthed bottle in which the ethylenediamine and the 1-adamantanamine were mixed, and was stirred strongly, thereby preparing raw material solution. Molar ratios of the respective components of the raw material solution were 1-adamantanamine/$SiO_2$=0.016 and water/$SiO_2$=21. Thereafter, the wide-mouthed bottle including the raw material solution was set to a homogenizer, and the raw material solution was stirred for 1 hour. After arranging the porous body 9, to which the DDR-type zeolite seed crystals were adhered in (3-2), into a stainless pressure resistant container 65 having a fluororesin inner tube with an internal volume of 300 ml, the prepared raw material solution (sol 67) was added therein, and they were put into the drier 68 so as to be subjected to heat treatment (hydrothermal synthesis) at 138° C. for 30 hours. The obtained product was washed with water, and was subsequently dried at 80° C. A nitrogen permeance at differential pressure of 0.3 MPa (0.4 MPa on a high pressure side and 0.1 MPa on a low pressure side) was measured. The nitrogen permeance at the differential pressure of 0.3 MPa is shown in Table 2.

(3A-4) Removal of Structure Directing Agent

The coated membrane was heated in the air atmosphere at 450° C. by an electric furnace for 50 hours so as to remove the 1-adamantanamine that was the structure directing agent in the pores by combustion, thereby obtaining the DDR-type zeolite membrane which did not contain the structure directing agent (separation membrane structure 1). The value of ($CF_4/CO_2$) obtained by dividing permeance of $CF_4$ measured at differential pressure of 0.1 MPa (0.2 MPa on the high pressure side and 0.1 MPa on the low pressure side) by permeance of $CO_2$ measured at differential pressure of 0.1 MPa (0.2 MPa on the high pressure side and 0.1 MPa on the low pressure side) is shown in Table 2.

Example 8

(3B) Formation of AEI-type Zeolite Membrane

In Example 8, an AEI-type zeolite membrane was formed as the zeolite membrane 33 on the inner wall surfaces 4s of the cells 4 of the porous body 9.

(3B-1) Production of Seed Crystal

After putting 6.15 g of aluminum triisopropoxide (produced by Kanto Chemical Co., Inc.) into an airtight container of 100 ml which was made of fluororesin, 40.07 g of tetraethyl ammonium hydroxide of 35% (produced by Sigma-Aldrich Co. LLC.) was added and stirred. Thereby, the aluminum triisopropoxide was dissolved into the tetraethyl ammonium hydroxide completely. Then, 20 g of pure water was added into the obtained solution, and the solution was stirred further. Thereafter, 10.98 g of phosphoric acid of 85% (produced by Sigma-Aldrich Co. LLC.) was added by being dripped with a spuit slowly. After the dripping, the spuit was rinsed with 2.80 g of pure water, and the liquid after the rinse was added into the airtight container. Subsequently, the stirring was continued for about 120 minutes, thereby obtaining a transparent raw material solution. Incidentally, the tetraethyl ammonium hydroxide is a structure directing agent.

Next, synthesis of AEI-type zeolite crystal powder (seed crystals) was carried out. More specifically, 80 g of the raw material solution was put into a stainless pressure resistant container having a fluororesin inner tube with an internal volume of 100 ml. Then, the raw material solution in the container was heated (subjected to hydrothermal synthesis) at 150° C. for 20 hours in a state of standing still. After the hydrothermal synthesis, the solution in which the AEI-type zeolite seed crystals were dispersed was collected, and was washed by repeating process twice, where the process includes: adding pure water; and carrying out centrifugal separation. A part of the obtained solution was dried at 80° C. overnight, thereby obtaining a dry powder (AEI-type zeolite seed crystals). A crystal phase of the obtained powder was identified as the AEI-type zeolite by XRD measurement (powder X-ray diffraction measurement).

(3B-2) Seeding (Particle Adhering Process)

By dispersing the AEI-type zeolite seed crystals into water (dispersing medium for seeding slurry), the seeding slurry (seed crystal slurry) was produced. A concentration of the AEI-type zeolite seed crystals was 0.23% by mass. The seeding slurry was poured into through holes (the cells) of the monolith shaped porous body, so that the inner wall surfaces of the through holes were coated with the seeding slurry. Thereafter, by allowing air at room temperature to flow into the through holes under a condition of wind speed of 2 m/s to 7 m/s for 30 minutes, the seeding slurry which coats the wall surfaces in the through holes was dried. The above-described operations were repeated twice in total, thereby obtaining the porous body in which the AEI-type zeolite seed crystals were adhered to the inner wall surfaces of the through holes. The seed crystal diameter and the adhered amount of the adhered seed crystals and the pore diameter of the porous body and the value of (seed crystal diameter/pore diameter of the porous body) are shown in Table 1.

(3B-3) Membranation (Membrane Formation Process)

After putting 4.72 g of aluminum triisopropoxide (produced by Kanto Chemical Co., Inc.) into a fluororesin container, 30.71 g of tetraethyl ammonium hydroxide of 35% (produced by Sigma-Aldrich Co. LLC.) was added and stirred. Thereby, the aluminum triisopropoxide was dissolved into the tetraethyl ammonium hydroxide completely. Then, 43 g of pure water was added thereto and stirred further. Thereafter, "solution obtained by diluting 8.41 g of phosphoric acid of 85% (produced by Sigma-Aldrich Co. LLC.) with 12 g of pure water" was added by being dripped with a spuit slowly. Subsequently, the spuit was rinsed with 101.17 g of pure water, and the liquid after the rinse was added. Thereafter, the stirring was continued for about 120 minutes, thereby preparing transparent membrane-forming raw material solution.

The porous body to which the seed crystals were adhered was arranged in a stainless pressure resistant container having a fluororesin inner tube with an internal volume of 300 cm$^3$, and the membrane-forming raw material solution was poured therein, which was subjected to heat treatment (hydrothermal synthesis) at 150° C. (synthesis temperature) for 30 hours (a synthesis time). Thereby, the AEI-type zeolite membrane was formed on the wall surfaces in the through holes of the porous body. Thereafter, the porous body on which the AEI-type zeolite membrane was formed was taken out; was washed with water; and was then dried at 80° C. for 48 hours. A nitrogen permeance at differential pressure of 0.3 MPa (0.4 MPa on the high pressure side and 0.1 MPa on the low pressure side) was measured. The nitrogen permeance at the differential pressure of 0.3 MPa is shown in Table 2.

(3B-4) Removal of Structure Directing Agent

The AEI-type zeolite membrane containing the structure directing agent, which was obtained in (3B-3), was subjected to heat treatment at 400° C. for 10 hours. By this heat treatment, the tetraethyl ammonium hydroxide that was the structure directing agent contained in the AEI-type zeolite membrane was removed by combustion, thereby obtaining the AEI-type zeolite membrane which did not contain the structure directing agent (separation membrane structure 1). The value of ($CF_4/CO_2$) obtained by dividing permeance of $CF_4$ measured at differential pressure of 0.1 MPa (0.2 MPa on the high pressure side and 0.1 MPa on the low pressure side) by permeance of $CO_2$ measured at differential pressure of 0.1 MPa (0.2 MPa on the high pressure side and 0.1 MPa on the low pressure side) is shown in Table 2.

(4) Pervaporation (PV) Test

Figure 5:
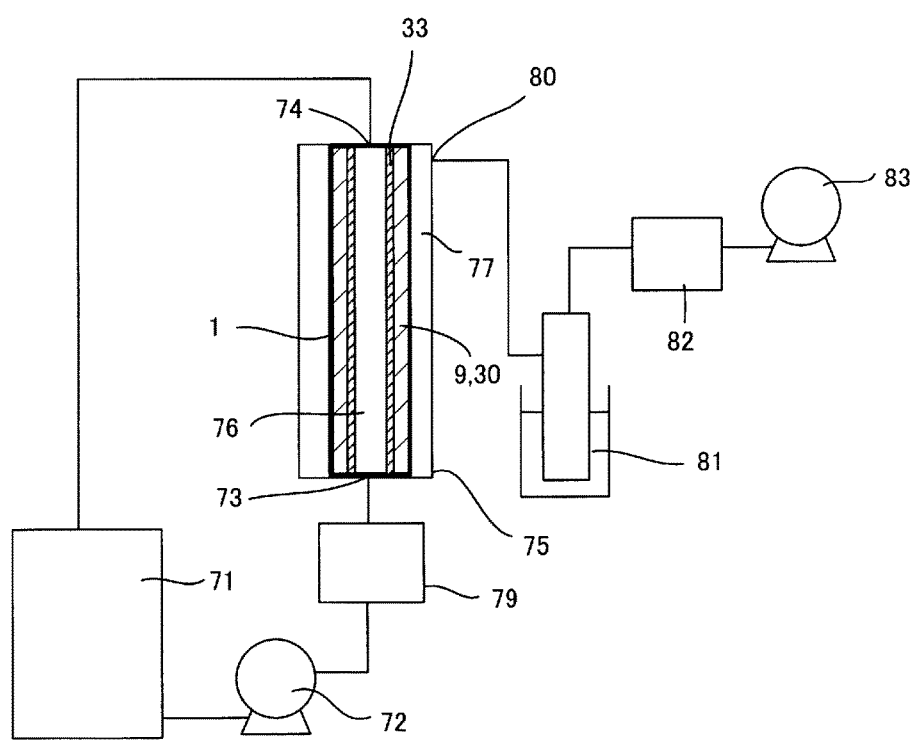
FIG. 5 is a schematic diagram that illustrates a whole of a testing device for carrying out a pervaporation test.

FIG. 5 is a schematic diagram that illustrates a whole of a testing device for carrying out a pervaporation test. A SUS module 75 had a structure in which the separation membrane structure 1 with the zeolite membrane 33 formed therein was installed in a cylindrical outside container that was made of SUS. An internal space of the SUS module 75 was partitioned into a raw material-side space 76 and a permeation-side space 77 by the zeolite membrane 33. Moreover, a supplied liquid introducing port 73 and a supplied liquid discharging port 74 were formed so as to communicate with the raw material-side space 76. Further, a permeated vapor collecting port 80 for discharging permeated vapor to the outside was formed in an upper end portion of the permeation-side space 77.

Acetic acid solution of 90% that was put in a raw material tank 71 was heated at 90° C. A supplying pump 72 supplied raw material from the supplied liquid introducing port 73 into the raw material-side space 76 of the SUS (stainless steel) module 75, and returned the raw material discharged from the supplied liquid discharging port 74 into the raw material tank 71, thereby circulating the raw material. A flow rate of the raw material was checked by a flowmeter 79.

By reducing pressure on the porous body 9 (substrate 30) side from the zeolite membrane 33 (permeation-side space 77) to 100 Torr by a vacuum pump 83, the permeated vapor that permeated the zeolite membrane 33 and was discharged from the permeated vapor collecting port 80 was collected by a liquid $N_2$ trap 81. A degree of vacuum in the permeated-side space 77 was controlled by a pressure controller 82.

The acetic acid permeance and the acetic acid concentration on the permeation side are shown in Table 2. An allowed value of the acetic acid concentration on the permeation side varies according to a purpose of the separation, and if the allowed value is 1% or less, an applicable range becomes wide, and thus, the zeolite membrane 33 can be considered as a high-performance separation membrane.

TABLE 2

| | Test | | | |
|---|---|---|---|---|
| Sample | Nitrogen Permeance at Differential Pressure of 0.3 MPa [NL/m$^2$minkPa] | Ratio of Permeance at Differential Pressure of 0.1 MPa ($CF_4/CO_2$) [—] | Acetic Acid Permeance [μmol/m$^2$sPa] | Acetic Acid Concentration on the Permeation Side [%] |
| Comparative Example 1 | 0.00032 | 0.02505 | 0.0019 | 2.57 |
| Example 1 | 0.00001 | 0.00062 | 0.0008 | 0.20 |
| Example 2 | 0.00013 | 0.00025 | 0.0010 | 0.19 |
| Example 3 | 0.00001 or less | 0.00202 | 0.0002 | 0.20 |
| Example 4 | 0.00001 or less | 0.00049 | 0.0002 | 0.23 |
| Example 5 | 0.00001 | 0.00390 | 0.0010 | 0.29 |
| Example 6 | 0.00001 or less | 0.00049 | 0.0003 | 0.23 |
| Example 7 | 0.00009 | 0.00932 | 0.0027 | 0.56 |
| Example 8 | 0.00001 or less | 0.00023 | 0.0001 | 0.03 |

In Examples 1 to 8, the ratios of the permeances ($CF_4/CO_2$) at the differential pressure of 0.1 MPa were small, and satisfactory results were obtained about the acetic acid permeance and the acetic acid concentration on the permeation side. After the test, the crystal phase was identified by X-ray diffraction, thereby confirming that the crystal phase was the DDR-type zeolite in Examples 1 to 7 and Comparative Example 1, and was the AEI-type zeolite membrane in Example 8. Moreover, fracture surfaces were observed with a scanning electron microscope, both of membrane thicknesses of the DDR-type zeolite membrane and the AEI-type zeolite membrane were 5 μm or less.

Since $CO_2$ is a component that permeates both of pores and defects, the permeance of $CO_2$ is useful for estimating a permeance of a component that permeates both of pores and defects similarly. On the other hand, since $CF_4$ is a component that permeates only defects, the permeance of $CF_4$ is useful for estimating a permeance of a component that permeates only defects similarly. In particular, in the separation of a liquid mixture, by estimating a separation performance with the components such as $CO_2$ and $CF_4$ which are gas at room temperature and at 1 MPa or less, the drying process and the like after the evaluation can be omitted, so that the performance evaluation process can be much easier than performance evaluation with liquid.

INDUSTRIAL APPLICABILITY

According to the method for manufacturing a zeolite membrane of the present invention, a zeolite membrane with fewer defects can be formed. The zeolite membrane of the present invention can be used for the separation of mixed liquid or the like.

DESCRIPTION OF REFERENCE NUMERALS

1: separation membrane structure,
1s: seal portion,
2, 2a, 2b: end face,
3: partition wall,
4: cell,
4s: inner wall surface,
6: circumferential surface,
9: porous body,
30: substrate,
33: zeolite membrane,
51: housing,
52: fluid inlet,
53, 58: fluid outlet,
54: seal material,
62: wide-mouth funnel,
63: cock,
64: slurry,
65: pressure resistant container,
67: sol,
68: drier,
71: raw material tank,
72: supplying pump,
73: supplied liquid introducing port,
74: supplied liquid discharging port,
75: SUS module,
76: raw material-side space,
77: permeation-side space,
79: flowmeter,
80: permeated vapor collecting port,
81: liquid $N_2$ trap,
82: pressure controller,
83: vacuum pump.

The invention claimed is:

1. A zeolite membrane having oxygen eight-membered rings, wherein a value obtained by dividing a permeance of $CF_4$ by a permeance of $CO_2$ is 0.015 or less.

2. The zeolite membrane having oxygen eight-membered rings according to claim 1, wherein an $N_2$ permeance in a state of containing a structure directing agent is 0.001 $NL/(m^2 \cdot min \cdot kPa)$ or less.

3. The zeolite membrane having oxygen eight-membered rings according to claim 1, which is a DDR-type zeolite membrane or an AEI-type zeolite membrane.

4. A method for manufacturing a zeolite membrane, comprising: subjecting a porous body to heat treatment at 400° C. or more in the presence of oxygen as pretreatment, before adhering zeolite seed crystals to a surface of the porous body; and subsequently adhering the zeolite seed crystals to the porous body so as to manufacture the zeolite membrane.

5. The method for manufacturing a zeolite membrane according to claim 4, comprising: storing the porous body under an environment of humidity of 30% or more for 12 hours or more after the heat treatment; and subsequently adhering the zeolite seed crystals to the porous body.

6. The method for manufacturing a zeolite membrane according to claim 4, comprising removing a structure directing agent from the zeolite membrane of which $N_2$ permeance in a state of containing the structure directing agent is 0.001 $NL/(m^2 \cdot min \cdot kPa)$ or less.

7. The method for manufacturing a zeolite membrane according to claim 4, wherein the zeolite membrane is a zeolite membrane having oxygen eight-membered rings.

8. The method for manufacturing a zeolite membrane according to claim 7, wherein, after adhering more than 0.05 $g/m^2$ of zeolite seed crystals having oxygen eight-membered rings to the surface of the porous body on which the zeolite membrane having oxygen eight-membered rings is to be formed, the zeolite membrane having oxygen eight-membered rings is formed in a raw material solution that contains: any of (a) a silica source and water, (b) a silica source, an alumina source and water, (c) an alumina source, a phosphorus source and water, and (d) a silica source, an alumina source, a phosphorus source and water; and the structure directing agent.

9. The method for manufacturing a zeolite membrane according to claim 7, wherein the zeolite seed crystals having oxygen eight-membered rings, of which average particle diameter ranges from 1.5 times to 3.0 times of an average pore diameter on the surface of the porous body on which the zeolite membrane having oxygen eight-membered rings is to be formed, are adhered to the surface of the porous body so as to form the zeolite membrane having oxygen eight-membered rings.

10. The method for manufacturing a zeolite membrane according to claim 7, wherein the average pore diameter on the surface of the porous body on which the zeolite membrane having oxygen eight-membered rings is to be formed ranges from 70 nm to 150 nm, and the average particle diameter of the zeolite seed crystals having oxygen eight-membered rings ranges from 105 nm to 450 nm.

11. The method for manufacturing a zeolite membrane according to claim 4, wherein the zeolite membrane is a DDR-type zeolite membrane.

12. The method for manufacturing a zeolite membrane according to claim 4, wherein the zeolite membrane is an AEI-type zeolite membrane.

13. A method for evaluating a zeolite membrane having oxygen eight-membered rings, wherein defects of the zeolite membrane having oxygen eight-membered rings are evaluated by a value that is obtained by dividing a permeance of $CF_4$ by a permeance of $CO_2$.

* * * * *